United States Patent [19]

Perlman

[11] Patent Number: 4,908,215

[45] Date of Patent: Mar. 13, 1990

[54] HYPOCHLORITE COMPOSITIONS CONTAINING THIOSULFATE AND USE THEREOF

[75] Inventor: Daniel Perlman, Arlington, Mass.

[73] Assignee: Brandeis University, Waltham, Mass.

[21] Appl. No.: 274,016

[22] Filed: Nov. 21, 1988

Related U.S. Application Data

[63] Continuation-in-part of Ser. No. 836,694, Mar. 6, 1986, abandoned.

[51] Int. Cl.$^4$ ............................................. A61K 33/14
[52] U.S. Cl. ................................... 424/661; 514/970; 514/973; 252/106
[58] Field of Search ............... 424/149, 150, 661, 667; 514/970, 973; 252/106

[56] References Cited

U.S. PATENT DOCUMENTS

| | | | |
|---|---|---|---|
| 3,136,716 | 6/1964 | Kitter | 424/149 |
| 3,253,979 | 5/1966 | Robson | 424/149 |
| 3,717,580 | 2/1973 | Echols et al. | 252/106 |
| 4,167,561 | 9/1979 | Lamberti et al. | 424/149 |

FOREIGN PATENT DOCUMENTS

| | | | |
|---|---|---|---|
| 1087955 | 10/1980 | Canada | 134/3 |
| 2094992 | 9/1982 | United Kingdom . | |

OTHER PUBLICATIONS

Lachman et al., The Theory and Practice of Industrial Pharmacy, 2nd Ed., 1976, p. 544.
Kamei et al., CA 98 #142104J, 1983.
Nikolaeva et al., CA 96 #161114n, 1982.
Hugo, Inhibition and Destruction of the Microbial Cell, Academic Press, London, 1971, Chapter 3E, pp. 137–183.

Primary Examiner—Douglas W. Robinson
Assistant Examiner—Zohreh A. Fay
Attorney, Agent, or Firm—Lorusso & Loud

[57] ABSTRACT

A one step process providing timed exposure to a substantially constant concentration of hypochlorite disinfectant is described, said process being completed when the hypochlorite is destroyed in an autocatalytic reaction with thiosulfate. The hypochlorite lifetime is precisely controlled by adjusting the initial pH of an alkaline disinfection solution of thiosulfate and hypochlorite, said solution containing a molar ratio of between 0.25 and 0.75 moles of thiosulfate to 1.00 mole of hypochlorite. Subsequently, with gradual evolution of acid and decreasing pH, the acid-dependent autocatalytic oxidation of thiosulfate is accelerated. This consumes the hypochlorite in a brief time interval, terminating the disinfection process. Also included in said alkaline disinfection solution is an appropriate concentration of $Na_2HPO_4$ or other chemical which is unreactive with hypochlorite and allows said initially alkaline pH to substantially decrease, but which later becomes a functioning pH buffer, controlling the final pH of the hypochlorite-free, disinfected solution. Completion of the disinfection process which is accompanied by a substantial pH decrease can be visualized by including one or more pH-color indicators in the disinfecting solution.

26 Claims, 4 Drawing Sheets

HYPOCHLORITE COMPOSITIONS CONTAINING THIOSULFATE AND USE THEREOF

CROSS-REFERENCE TO RELATED APPLICATION

This application is continuation-in-part application of co-pending application Ser. No. 836,694, filed Mar. 6, 1986 now abandoned.

BACKGROUND OF THE INVENTION

The present invention relates to a chemical solution process for time-delayed destruction of hypochlorite. The solution disinfects, sterilizes, bleaches and cleans inanimate objects, surfaces, solutions and the like. The solution contains both thiosulfate and hypochlorite, preferably alkali metal or alkaline earth metal salts of hypochlorite, with the hypochlorite providing free chlorine for sterilization and disinfection until the thiosulfate consumes the hypochlorite.

Sodium, potassium, lithium, and calcium hypochlorites are well known for their disinfection and bleaching properties. The disinfecting properties are discussed in U.S. Pat. No. 3,717,580 to Echols et al., in Canadian Patent No. 1,087,955 to Sokol et al., in G.B. Patent No. 2.094,992 to Tanaka et al., and in U.S. Pat. No. 4,167,561 to Lamberti et al. wherein it is disclosed that the duration of exposure to hypochlorite solutions may be controlled by addition of certain chemical reducing agents to the hypochlorite solutions.

The use of citrates, malates and other hydroxycarboxylic acid reducing agents which react slowly with hypochlorite to destroy residual activity is disclosed in Echols et al. and Sokol et al. The addition of still other reducing agents to aqueous solutions either before or after the generation of hypochlorite in these solutions is disclosed in Tanaka et al. It is significant that Tanaka et al. place "alkali or alkaline metal salts of thiosulfuric acid such as sodium thiosulfate" in the category only appropriate for addition to hypochlorite after sterilization, consistent with prior art knowledge that thiosulfate is one of the agents know "to decompose or reduce the sodium hypochlorite to an innoxious state in extremely short time . . . " (Tanaka et al.). Lamberti et al, describe the use of a mixed solution containing an organic compound, alpha-hydroxy-beta sulfosuccinate and hypochlorite. With this mixture, the user can, at a desired time, lower the pH and heat the solution to substantially destroy the hypochlorite after a suitable disinfection interval.

Although Echols et al. describe a hypochlorite-containing solution which is self-inactivating, their system suffers from the expotential loss of hypochlorite activity during disinfection. This continuous loss of hypochlorite necessitates compensation with higher initial levels of hypochlorite than would otherwise be required if inactivation were time-delayed. A further disadvantage of the Echols et al. system for destroying hypochlorite is found in animal model studies which indicate that the reaction between hypochlorite and hydroxycarboxylic acids products physiologically irritating and perhaps toxic oxidation by-products thereby limiting the pharmaceutical usefulness of this process.

Although Lamberti et al. describe the advantages of a time-delayed system for the destruction of hypochlorite (maintaining a constant level of hypochlorite during disinfection), their mixed solution of hypochlorite and reducing agent must be heated and/or and pH-adjusted to destroy the hypochlorite. These usage steps may be inconvenient or even impossible to implement in many applications, eg. spraying or in processing large volumes.

Recently the use of sodium thiosulfate reducing agent was described in the rapid inactivation of residual hydrogen peroxide following disinfection (Ogunbiyi, Clinical & Experimental Optometry, 69.1: January 1986). This "post-disinfection" addition of thiosulfate is in agreement with its use by Tanaka et al and consistent with its high reactivity with strong oxidizing agents.

Prior to the present invention however, it was not appreciated that the reactivity of thiosulfate with hypochlorite could be appropriately reduced by increasing the pH of the mixture. Thus it was surprising to discover that a quantity of thiosulfate sufficient to destroy the hypochlorite in a disinfection or sterilization solution, could be initially combined in that hypochlorite-containing solution (prior to disinfection) and still permit the disinfection or sterilization process to occur. Furthermore, it was not appreciated that a pH-controllable autocatalytic oxidation of thiosulfate could be utilized to destroy hypochlorite following a time delay whose duration could be programmed by adjusting the original pH of the thiosulfate-hypochlorite mixture. It was also not appreciated that a narrow and defined range of thiosulfate:hypochlorite mole ratios constrain the above process. Finally it was not appreciated that a self-inactivating hypochlorite disinfection system, initiated at substantially alkaline pH, could be self-titrating to achieve a substantially neutral pH, by including in the reaction solution a chemical which, upon a pH decrease in the reaction solution, became a pH buffer.

The present process requires only the simple mixing of common inorganic chemicals, in proper proportions, at room temperature. This process, producing only simply non-toxic inorganic reaction products, is compatible with food and drug use.

SUMMARY OF THE INVENTION

A one-step process for disinfection, sterilization, bleaching, and cleaning of surfaces, solutions, and the like using hypochlorite, and more generally, chemical compositions for achieving time-delayed destruction of hypochlorite, using thiosulfate, has been invented. The process which requires only one initial mixing step, preferably utilizes an essentially unbuffered solution initially set at an appropriate alkaline pH, said solution containing appropriate proportions of sodium hypochlorite and sodium thiosulfate. Any stable non-toxic and soluble organic or inorganic chemicals capable of generating hypochlorite and thiosulfate are suitable for use in the present invention. The molar ratio of thiosulfate to hypochlorite must be set between 0.25 and 0.75 moles thiosulfate:1 mole hypochlorite for this time-delayed destruction of hypochlorite to occur. A chemical such as dibasic sodium phosphate which becomes a pH-stabilizing buffer only after the pH of the disinfection solution has substantially fallen (and the reaction time-delay has been achieved), is also included in the said solution. This chemical agent (also termed a "precursor to a buffer or pre-buffer") insures that the final pH of the disinfected solution is controlled (important for the subsequent utility of this solution).

It has been found that at an appropriate alkaline starting pH, the oxidation of thiosulfate to sulfate is slow, inducing the pH to decrease slowly and reproducibly as acid is produced in the sulfate-forming reaction. It has also been discovered that this pH decrease, in turn autocatalytically accelerates the thiosulfate to sulfate oxidation process, culminating in the major portion of hypochlorite disinfectant being rapidly consumed, often in a matter of seconds, at the end of the disinfection process. The lifetime of the hypochlorite in solution can be set, independent of the concentration of the hypochlorite and thiosulfate reactants, by adjusting the alkaline starting pH of the initial disinfection solution. Thus the starting pH for a disinfection employing 2000 ppm hypochlorite is set at about 10.7 while that employing 250 ppm hypochlorite is set at about 10.1 to achieve hypochlorite destruction after a 20 minute lifetime in room temperature solutions. The present invention can be used in one-step self-contained sterilization of solutions and equipment including sealed pressurized aerosol solutions, bottled water, physiological saline, surgical equipment and the like. The process and compositions described herein can be safely used in juxtaposition with foods and drugs because the chemical products produced in this chemical process are known to be nontoxic. The process and compositions described herein can also be utilized for timed destruction of hypochlorite in general. For example, control of hypochlorite contact time and removal of residual hypochlorite odor are achieved by this process and can be used to control bleaching of fabrics, cleaning and disinfection of hospital equipment and medical devices such as dental prostheses and contact lenses and in a variety of other applications.

If one or more pH color indicators having appropriate pH-transition ranges is included in the disinfection solutions of the present invention, a visual indication of the completion of the disinfection process is obtained. That is, a color change can be used to witness the fall in pH accompanying destruction of remaining hypochlorite. The color indicators must be chemically unreactive with hypochlorite and are preferably non-toxic in the concentrations required for a visually detectable color change.

DETAILED DESCRIPTION OF THE INVENTION

Figure 1:
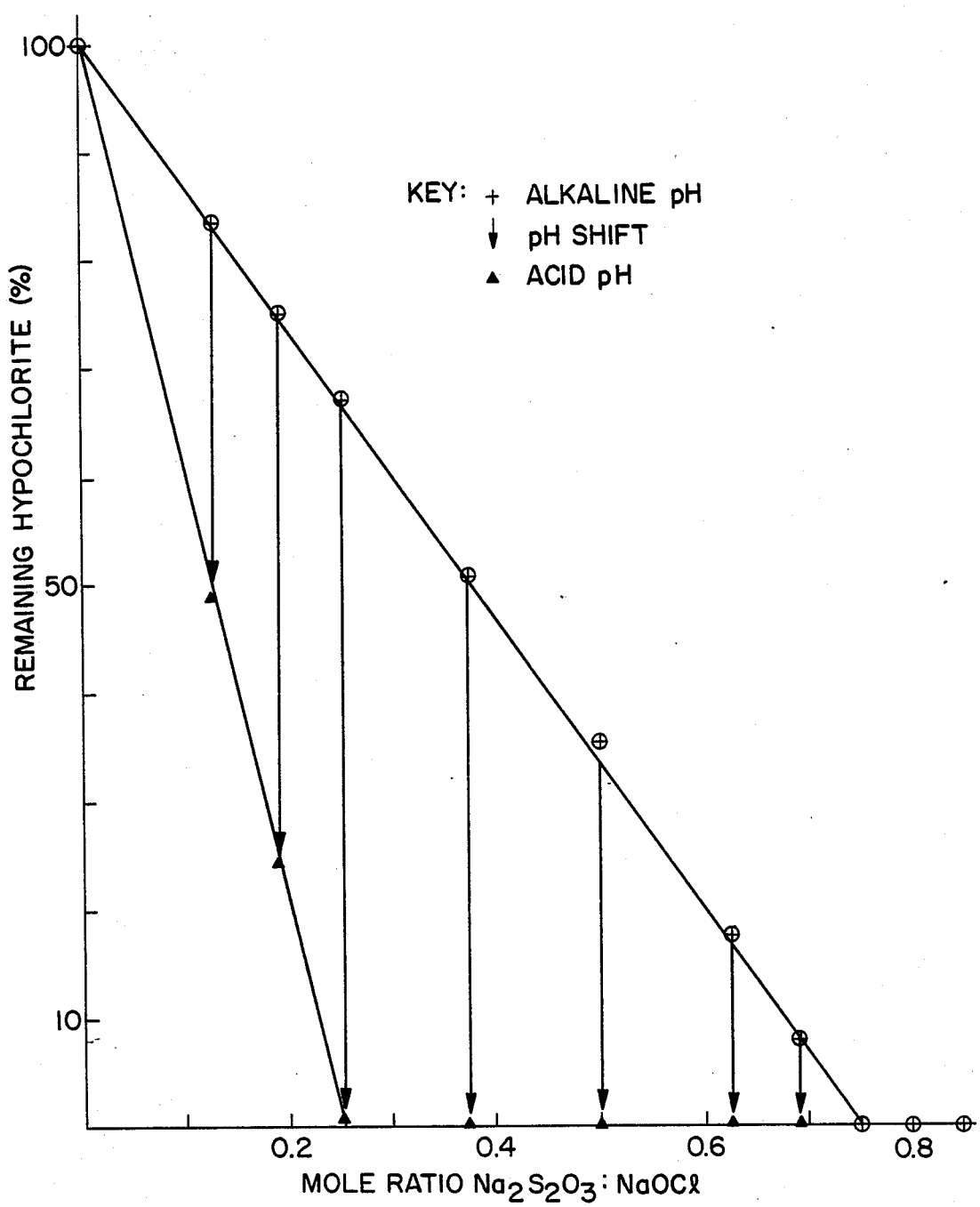
FIG. 1 is a graphical representation showing decreasing hypochlorite concentrations remaining in alkaline and acidic solutions with increasing molar ratios of sodium thiosulfate to sodium hypochlorite.

The solutions suitable in the practice of the present invention preferably contain; (i) an alkali-metal or alkaline-earth hypochlorite; (ii) an alkali-metal or alkaline-earth thiosulfate; and (iii) a chemical substance such as dibasic sodium phosphate which is unreactive with hypochlorite and which, while initially not functioning as a pH buffer, later becomes functional as a pH buffer after an alkaline mixture of hypochlorite and thiosulfate are reacted to produce acid causing the pH of said mixture to substantially decrease.

The present invention requires that the three above ingredients be present in certain relative and absolute concentrations and that they be combined at certain alkaline pHs, said pHs being a function of the concentration of hypochlorite, thiosulfate, and the duration of disinfection desired.

According to the chemical reaction equation:

$$Na_2S_2O_3 + 4NaOCl + H_2O \rightarrow Na_2SO_4 + 2NaCl + 2HCl \quad \text{(Equation I)}$$

0.25 moles of thiosulfate are sufficient to destroy 1 mole of hypochlorite. This stoichiometry has been confirmed. Reaction I appears to occur instantaneously at neutral and acidic pH but more slowly at alkaline pH. In fact with pHs above 8.5 it is possible to discern two or more stages to reaction (I). The first stage of thiosulfate oxidation is observed to occur instantaneously regardless of pH, consuming approximately Δ of the reactive capacity of the thiosulfate by reaction with the hypochlorite. Measurements of pH before and after mixing the reactants show that alkali is produced in this first stage of reaction. One of the reactions which is believed to contribute to this initial alkali production consumes only ⅛ of the reaction capacity of thiosulfate:

$$2Na_2S_2O_3 + NaOCl + H_2O \rightarrow Na_2S_4O_6 + NaCl + 2NaOH \quad \text{(Equation II)}.$$

Subsequently, the second stage of the thiosulfate oxidation occurs very slowly at a pH of 9 or above, and pH measurements made during this stage show that acid is being produced. It has herein been observed, however, that as the pH of a thiosulfate-hypochlorite reaction solution (containing for example a ratio of 0.25 moles thiosulfate:1.00 mole hypochlorite) falls below about pH 8.5-9, the oxidation of thiosulfate to sulfate rapidly accelerates. This phenomenon is dramatically demonstrated in an unbuffered or weakly buffered alkaline solution of thiosulfate and hypochlorite mixed together in mole ratios of between 0.25-0.75 moles thiosulfate:1.00 mole hypochlorite. If for example 2 mM thiosulfate and 7 mM hypochlorite, each at approximately pH 9, are mixed together, the pH jumps to approximately 10.3 in the first stage of thiosulfate oxidation which produces alkali. However, as acid is slowly produced according to equation (I) the pH slowly falls. Subsequently, the reaction rate increases and the pH falls more rapidly in an autocatalytic fashion. Without any agent to arrest the pH decrease, the solution becomes significantly acidic as illustrated in Example 2, and the reaction rapidly progresses toward completion. In co-pending U.S. patent application Ser. No. 836,694 filed Mar. 6, 1986, examples are provided demonstrating the relative rates of thiosulfate oxidation by hypochlorite as a function of pH. For example, at pH 9.0 destruction of 7 mM hypochlorite via reaction with 2 mM thiosulfate occurred in approximately 15 min while at pH 8.2 said destruction occurred in less than one minute. In these examples, the pHs in said oxidations were maintained constant throughout the reaction (unlike the present invention) by including an initial pH-stabilizing buffer such as a boric acid-sodium borate system buffer.

There are at least two disadvantages in maintaining constant pH throughout the thiosulfate-hypochlorite reaction process. First, as in the Echols et al. patent describing the reaction between hydroxycarboxylic acids and hypochlorite, the hypochlorite is most rapidly depleted near the beginning of the timed process rather than at the end. This early depletion diminishes the disinfection efficacy of the hypochlorite. Second, employing a certain fixed pH to obtain prescribed exposure to hypochlorite, subsequently limits the utility of the disinfected solution. Nevertheless, it is believed that the original discovery by Perlman (U.S. patent application Ser. No. 836,694 filed Mar. 6, 1986) describing the use of alkaline-buffered solutions to slow down an otherwise instantaneous reaction between thiosulfate and hypochlorite at neutral pH, may prove to be useful. As with the present invention, a controlled reaction between thiosulfate and hypochlorite requires that their mole ratio initially be between 0.25 to 1.0 and 0.75 to 1.0, respectively.

In the present invention however, a pH buffer is not included in the initial reaction solution and therefore the initial reaction pH is not maintained constant. Rather, the pH of the solution is allowed to fall to whatever level is finally desired, based on the desired usage of the hypochlorite-disinfecting solution. To arrest the falling pH at a desired level eg. pH 7.0, a chemical is included in the disinfection solutions such as a salt of sodium phosphate ie. $Na_2HPO_4$ whose pKa (7.2) is near the desired pH level, yet substantially below the initial pH of the disinfection solution. The said chemical is not initially a pH buffer, but it becomes a buffer after the pH of the reaction solution has substantially decreased to a value near the chemical's pKa. The choice of said chemical (also termed pre-buffer) is based on its pKa relative to the final pH desired and on the stability of the chemical in the presence of hypochlorite.

To begin a disinfection or sterilization reaction in a saline solution it is typical to add an alkaline sodium hypochlorite solution to a sodium thiosulfate-saline solution containing dibasic sodium phosphate. The starting pH after mixing is typically set between pH 8.5 and 11. The phosphate salt has essentially no buffering capacity in this range. As the pH falls below 8.5–9 the oxidation of thiosulfate rapidly accelerates. Without the phosphate salt, the completed reaction mixture becomes grossly acidic (e.g. pH 3.5 Example 2). However, addition of an appropriate concentration of the phosphate salt stabilizes the final pH at 7.2+0.5.

The discovery of conditions which permit a time-delayed autocatalytic reaction to occur between hypochlorite and thiosulfate, combined with the ability to pre-program the final pH of the disinfected solution provide a new self-neutralizing hypochlorite-based disinfection/sterilization method. This method is carried out with just a single operational step, ie. mixing the initial chemical components. The disinfection or sterilization concentration of hypochlorite, the lifetime of that hypochlorite in solution, and the final pH of the disinfected solution may be manipulated at will as is shown herein by the various Examples.

As previously indicated, an upper limit exists to the mole ratio of thiosulfate which can be combined in solution with hypochlorite to obtain the time-delayed reaction of the present invention. As detailed in Example 1, if a ratio of more than 0.75 moles thiosulfate:1 mole hypochlorite is utilized, all of the hypochlorite is instantaneously destroyed (regardless of the solution pH). Therefore, only by selecting a ratio of between 0.25 and 0.75 moles thiosulfate:1 mole hypochlorite can the the rate of hypochlorite destruction be controlled. This control is easily achieved by varying the initial pH of the reaction solution.

Within the pH range of about 8–12, thiosulfate and hypochlorite may be initially mixed in the practice of the present invention. This initial pH is very important in determining the lifetime of a particular concentration of hypochlorite in solution (see Example 3). An initial pH level of about 8.5–11 is preferred for most general uses. The final pH of the disinfected solution following destruction of all hypochlorite by thiosulfate is about 3 to about 8.5. The final pH is preferably controlled at about 6 to 8. Only the initial pH of the solution need be measured and adjusted with acid or alkali such as HCl of NaOH because the final pH may be reproducibly controlled by the composition and pH of the initial solution.

The temperature of the disinfection or sterilization solution should also be monitored, and if appropriate, should be regulated. It has been determined that the rate of thiosulfate oxidation which determines the hypochlorite lifetime in solution, is directly affected by temperature. At 0° C. the rate of thiosulfate oxidation is approximately half, and at 37° C. approximately twice that rate measured at room temperature (23° C.) for solutions having pHs between 9 and 10.

The disinfection or sterilization solution typically includes a chemical which is a precursor to a buffer (also termed a "pre-buffer") and which becomes a pH buffer only in the course of the pH decrease accompanying hypochlorite destruction. Such chemicals which become effective pH buffers in the final pH range of the present invention and which are unreactive with hypochlorite, include dibasic alkali-metal phosphates such as $Na_2HPO_4$ and $K_2HPO_4$ and alkali-metal borates such as $Na_2B_4O_7$ and $K_2B_4O_7$, and alkali-metal carbonates such as $Na_2CO_3$ and $K_2CO_3$. The concentration of said chemicals chosen for final pH stabilization depends upon the concentration of hypochlorite selected for disinfection, (thereby determining the amount of acid liberated in the destruction of the hypochlorite) and the desired final pH. It has been empirically determined that when 7 mM sodium hypochlorite (approximately 500 ppm active chlorine) is mixed with 2 mM sodium thiosulfate at an initial pH of 10.0–10.5, the addition of 10 mM $Na_2HPO_4$ forms an appropriate and sufficient pH-stabilizer following destruction of the hypochlorite (final pH, approximately 7.0). However, higher or lower $Na_2HPO_4$ concentrations may be used to establish higher or lower final pHs respectively. Similarly, approximately 2.5 mM $Na_2B_4O_7$ may be utilized in this role. If however, a ratio of greater than 2 mM thiosulfate: 7 mM hypochlorite is employed, a corresponding decrease in acid production is observed (higher final pH, see Table 2) and the amount of dibasic phosphate or borate salt may be correspondingly reduced. The chemical basis for this decreased acid production could be that higher ratios of thiosulfate: hypochlorite in the disinfection solution produce more tetrathionate ($S_4O_6^{2-}$) relative to sulfate ($SO_4^{2-}$), resulting in a net decrease in acid production (see Equation II). Phosphate or borate pre-buffer concentrations have been successfully scaled upward and downward, in keeping with the concentration of hypochlorite employed during disinfection (see Table 3). With the present invention, concentrations of pre-buffers ranging from 0.1 mM to 200 mM have proven useful. It is within the scope of the present invention to employ other chemical agents which are unreactive with hypochlorite besides dibasic phosphate salts and borate salts to stabilize the final pH of the solution following hypochlorite destruction.

Hypochlorite solutions contain both the hypochlorite anion and the undissociated hypochlorous acid species above and below pH 7 at which about three fourths of the hypochlorite is in the acid form. The term "hypochlorite" without designation of the cation as used herein refers to the acid form, the salt form, and mixtures of these forms. The term "thiosulfate" without designation of the cation as used herein refers to the salt forms of thiosulfate as well as to varied uncharacterized thiosulfate oxidation intermediate compounds formed by reaction of hypochlorite with thiosulfate, but excluding the terminal sulfate product itself ($SO_4^{2-}$). By this definition, all thiosulfates carry chemical reducing potential relative to hypochlorite.

The concentration of hypochlorite in a disinfecting solution (also termed a reaction solution or reaction mixture) ranges from a lower limit of about 4 ppm available chlorine (approximately 0.00005 molar hypochlorite) to about 5,000 ppm available chlorine (approximately 0.07 molar hypochlorite). The concentration of thiosulfate ranges from about 0.000012 molar to about 0.05 molar. The molar ratio of thiosulfate which can initially be mixed with hypochlorite in a disinfection solution of the present invention may vary from about 0.25 to 1 to about 0.75 to 1.

In the practice of the present invention it is convenient to titrate a standardized alkaline hypochlorite solution such as a 5.25% by weight hypochlorite solution to a standard alkaline pH value such as 9.0 or 10.0. This titration facilitates achieving a predictable initial pH in the disinfecting solution when the hypochlorite is added to the other ingredients. The initial pH chosen for the disinfecting solution is based on the initial concentrations of hypochlorite and thiosulfate as well as the hypochlorite lifetime desired by the user of the present invention. This said initial pH is empirically determined and may be set by adding a pre-determined amount of acid or alkali such as HCl or NaOH when the disinfecting solution is initially constituted. Examples 3, 4 and 5 illustrate various choices of initial pH and their effect on hypochlorite lifetime, given various hypochlorite and thiosulfate concentrations. Stabilization of the final pH in the disinfection or sterilization solution following destruction of the hypochlorite is achieved by addition of a chemical which is a precursor to a buffer to the initially constituted disinfecting solution. This said chemical must have pH-buffering capacity at said final pH but must have little or no pH-buffering capacity at the pH of said initially constituted solution. Although final pHs ranging from approximately 3 to about 9 are encompassed by the present invention it is often desirable to achieve approximately neutral pH in a disinfected solution. The addition of alkali-metal dibasic phosphates or alkali-metal borates to the initially constituted disinfecting solution achieves said neutral pH. As required, the simple inorganic phosphate salts, like the borate salts, are unreactive ie. chemically stable in the presence of hypochlorite. With pKa values 2.1, 7.2 and 12.3 (for the phosphate's three acid dissociations) there is little to no buffering in the pH 8.5-11 range in which the slow thiosulfate oxidation of the present invention occurs, while there is excellent buffering at pH 7. Given the acid released in the oxidation of thiosulfate to sulfate (reaction I), appropriate concentrations of dibasic phosphate are selected to achieve a desired final pH near 7.

It has been empirically determined, as illustrated in Example 5, that appropriate phosphate concentrations can be chosen by scaling the phosphate concentration to the concentration of the hypochlorite and thiosulfate which are reacting to produce the acid. For example, a concentration of 10 mM $Na_2HPO_4$ (0.14% by weight) is appropriate for mixing with 7 mM hypochlorite and 2 mM thiosulfate, to achieve a pH of approximately 7.0 following destruction of hypochlorite.

The solutions of the present invention are stable against chemical decomposition over long periods of time at room temperature. Thiosulfate solutions are best maintained pH-neutral to slightly alkaline to prevent autodecomposition, while hypochlorite solutions are best maintained in alkaline concentrated form (pH 11 or greater) to minimize loss of hypochlorite through volatilization of the HOCl acid form. Shortly before using the concentrated hypochlorite solution, it is often convenient to lower its pH to 9-10.

It has been empirically determined that many different liquid, powder and tablet formulations of hypochlorites, thiosulfates as well as precursors to buffers which become pH buffers (in the course of the chemical process of this invention) may be constituted to generate the process of the present invention. It has also been empirically determined that virtually any hypochlorite-generating chemical compound whose oxidation-reduction reaction with thiosulfate creates products which are non-toxic to humans is suitable for use in the present invention. For many uses, alkali-metal or alkaline-earth metal hypochlorites are preferred, but any of the so-called "available chlorine compounds" which all produce hypochlorous acid, HOCl, and hypochlorite anion, $OCl^-$, are functional and may be used in the present invention. The available chlorine compounds include elemental chlorine, hypochlorite bases, salts, and acids as well as N-chloro compounds. These respective compounds product hypochlorous acid as follows:

$$Cl_2 + H_2O \rightarrow HOCl + H^+ + Cl^- \quad (1)$$

$$NaOCl + H_2O \rightarrow HOCl + Na^+ + OH^- \quad (2)$$

$$RR'NCl + H_2O \rightarrow RR'NH + HOCl \quad (3)$$

In alkaline solutions the HOCl dissociates to yield the hypochlorite anion. Briefly, but more specifically for the three reactions above, when elemental chlorine dissolves in water above pH 4, half of the chlorine produces HOCl, the remainder producing HCl. For the second reaction above, a variety of common industrial chemicals produce the hypochlorite anion by direct dissociation in aqueous solution. These include sodium hypochlorite, calcium hypochlorite, lithium hypochlorite, chlorinated trisodium phosphate and bleaching powder. For the third reaction above, a variety of N-chloro, (ie. nitrogen-chlorine) bonded chemicals exist including chloramines, chloramides, chloramines, chlorimides, chlorosulfonamides and chlorohydantoins (such as 1,3-dichloro-5, 5 dimethylhydantoin) all of which yield hypochlorous acid and/or hypochlorite anion to varying degrees depending upon the particular hydrolysis constants for the compounds and the solution pH. Since the generation of $OCl^-$ from N-chloro compounds is favored by alkaline pH, the use of these compounds is appropriate and compatible with the initially alkaline pH required to achieve the time-delayed inactivation of hypochlorite described in the present invention.

For the purpose of utilizing the process of the present invention in cleaning as well as disinfection of articles and surfaces (such as surgical equipment, hospital surfaces and the like), certain wetting agents, surfactants and detergents (collectively termed detergent) can be included in the disinfecting solutions of this invention. Any detergent which is substantially unreactive with hypochlorite is suitable for such use. These detergents include anionic, nonionic, and quaternary species.

Example of anionic detergents which can be used in mixture with the components of the present invention include alkali-metal salts of fatty acid mixtures, ie. soaps. Other anionic detergents include alkylsulfates, alkyl monoglyceride sulfates, alkylpolyoxyethylene sulfates, alkylbenzene sulfonates and acylsarcosinates. Examples of useful nonionic detergents include 1-octylphenol and dodecyl methyl sulfoxide. Examples of quaternary detergents which are useful include alkylammonium-propane-sulfonates such as 3-(N,N-dimethyl-N-dodecylammonio)-propane-1-sulfonate.

For the purpose of visualizing completion of the process of the present invention and in particular, the final stage of chemical destruction of hypochlorite, said destruction being accompanied by a substantial pH decrease, one or more pH color indicators (collectively termed pH indicator) is included in the disinfection solution. The pH indicator must be substantially unreactive with hypochlorite. Examples of such an indicator include phenolphthalein and naphtholphthalein.

In accordance with the process of the present invention, if a solution and its container are to be disinfected or sterilized, for example in the case of an aerosol can holding a physiological concentration of aqueous saline (approximately 0.9% by weight NaCl), the can is filled with a saline solution at an appropriate pH, containing appropriate concentrations of an alkali-metal thiosulfate, an alkali-metal dibasic phosphate and optionally a detergent as set forth above. A relatively small proportional volume of hypochlorite at an appropriate concentration and pH is then added to start the disinfection process. The aerosol valve assembly is promptly inserted into the can and sealed in place. The can is shaken and the aerosol valve is then activated so that the valve assembly fills with and dispenses a small volume of disinfecting solution. This last step insures disinfection of all surfaces within the aerosol can in addition to the solution. After the desired disinfection treatment whose duration is programmed by the chemistry of the disinfection solution as herein described, the hypochlorite is completely destroyed and the disinfected or sterile solution is ready for use. The duration of disinfection treatments (ie. the time between hypochlorite addition to a disinfecting solution, and the destruction of 100% of the initial hypochlorite), has been successfully varied so as to be as short as 30 seconds and as long as 3 hours using the process of the present invention.

The invention is more fully described, in the following exmples which are illustrative, but are not be considered limitive of the invention.

EXAMPLE 1

Mole-ratio limits for acid-catalyzed destruction of sodium hypochlorite by sodium thiosulfate are disclosed.

An alkaline stock solution of NaOCl (5.25%) was diluted 1000-fold to obtain a 7.05 mM working concentration of NaOCl. The solution was adjusted to pH 10.5. Samples of this solution were reacted with increasing amounts of $Na_2S_2O_3$. Portions of these alkaline-reacted samples were assayed for residual NaOCl using iodimetry (see FIG. 1, samples denoted by + symbols) while other portions were acidified (final pH 6) prior to quantitating remaining NaOCl (samples denoted by symbols). Iodimetry consisted of preparing a 0.1M NaI solution, acidifying it shortly before use (0.1N final concentration HCl), transferring 0.75 ml aliquots of this solution to assay tubes, adding 0.25 ml of the solutions to be assayed for NaOCl, vortexing, and reading the optical density (OD) of the yellow iodine produced by oxidation. Depending upon the concentration range of NaOCl and iodine produced in an experiment, OD was monitored at either 450 nm, 465 nm or 485 nm. These readings could be compared using multiplier factors of 1.00, 1.62 and 3.49 respectively.

The graph in FIG. 1 shows that alkaline solutions containing a mole ratio of sodium thiosulfate to sodium hypochlorite of between 0.25 and 0.75 can be acidified resulting in the inactivation of residual hypochlorite. The 0.25 minimum mole ratio is consistent with the stoichiometry of Equation (I) shown in this text. The 0.75 mole ratio representing a three-fold stoichiometric excess, is an empirical upper limit for this process. Given equation (I), this upper limit implies that ⅓ (0.25/0.75) of the total reducing power of $Na_2S_2O_3$ is consumed, regardless of the pH, upon mixing with NaOCl.

EXAMPLE 2

The free-fall in pH accompanying hypochlorite inactivation is arrested by a precursor to a buffer in the reaction.

A 20 ml aqueous saline solution was prepared containing 125 mM NaCl, 2 mM $Na_2S_2O_3$, and 10 mM $Na_2HPO_4$ ("pre-buffer"). To this solution, 0.20 ml 5.25% NaOCl (titrated to pH 10.0 with HCl) was added yielding a final concentration of 7 mM NaOCl (approximately 500 ppm chlorine), producing a starting pH in the reaction of 10.31. During the reaction conducted at 23° C., the pH was monitored continuously (see curve 1, FIG. 2) and samples were removed for iodometry determination of residual NaOCl (see curve 2, FIG. 2) as described in Example 1. The amount of hypochlorite present in the reaction solution upon initial mixing has been defined as 100%. The hypochlorite concentration after mixing is approximately ⅓ less than initially added to the disinfection solution as shown in Example 1 and confirmed in this experiment as well.

Figure 2:
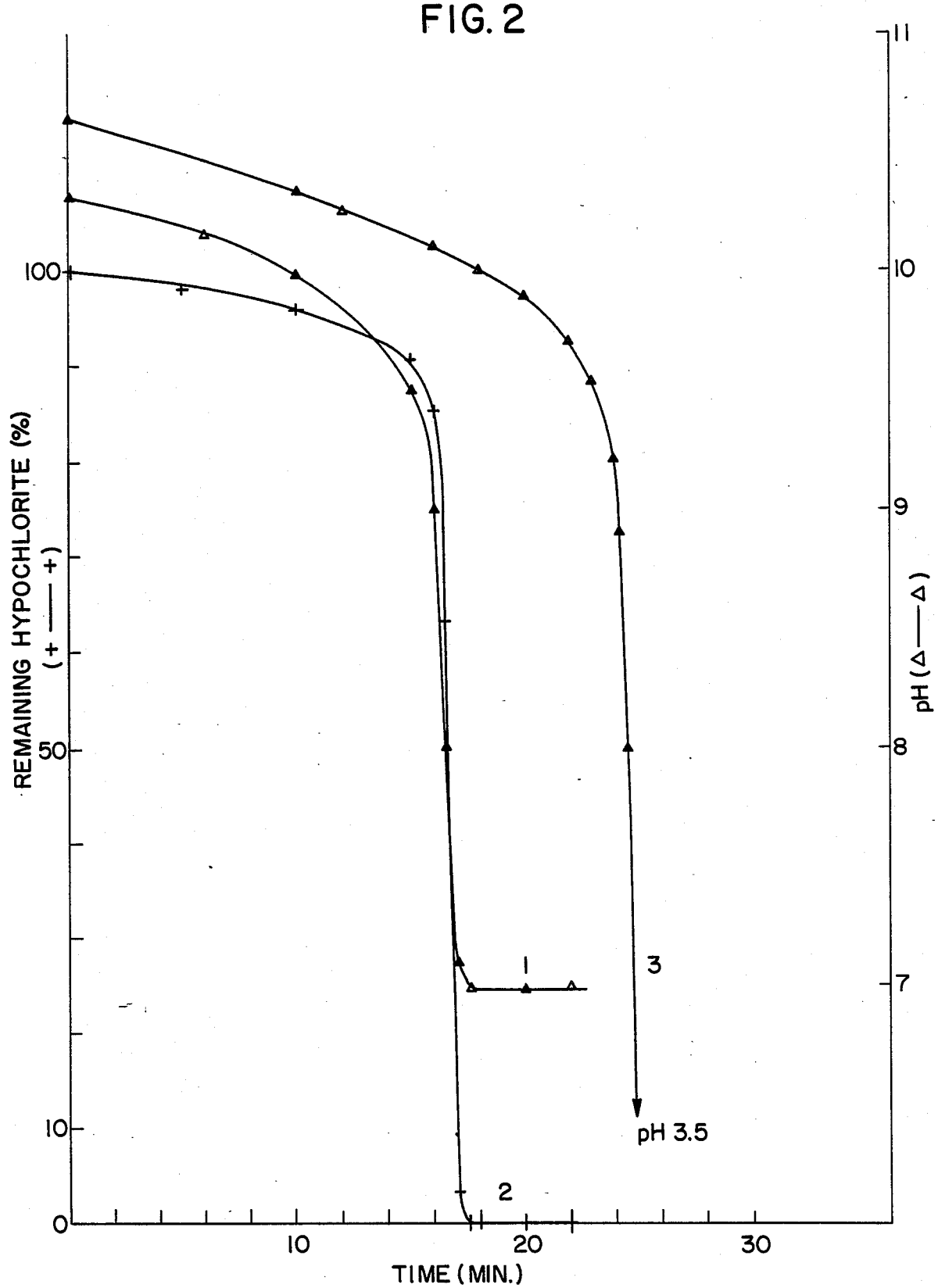
FIG. 2 is a graphical representation of the amount of active hypochlorite remaining in solution and the decrease in pH as a function of time for solutions either with or without dibasic sodium phosphate.

A parallel reaction solution identical to that above, but lacking the pre-buffer, was also prepared as a pH control experiment (see curve 3, FIG. 2). It is apparent that without the pre-buffer, the solution becomes highly acidic (pH 3.5) during the redox reaction and would not be immediately useful for many pharmaceutical uses.

EXAMPLE 3

Control of hypochlorite lifetime by varying the initial pH of a saline reaction mixture containing fixed concentrations of hypochlorite, thiosulfate and pre-buffer is shown.

Figure 3:
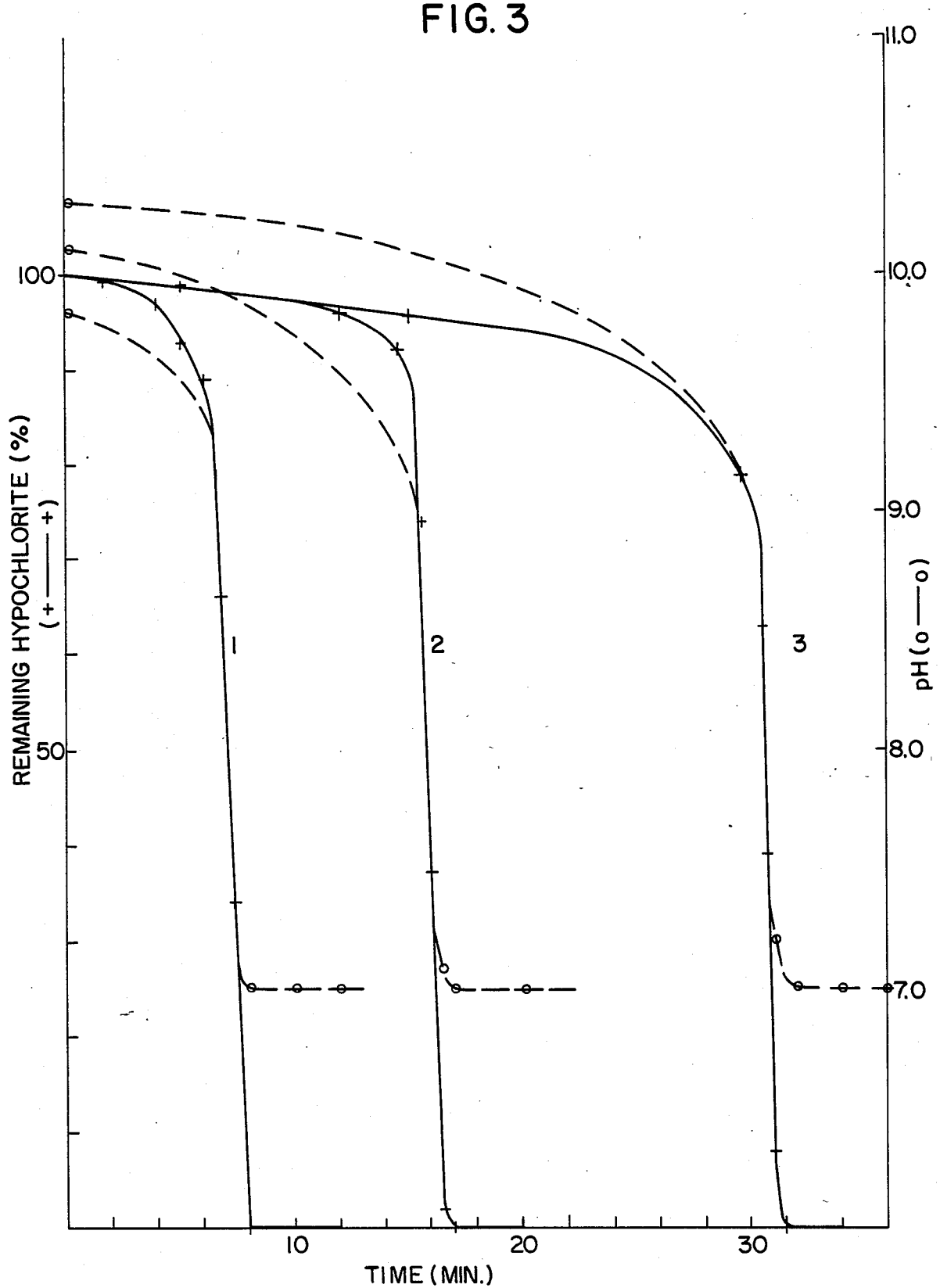
FIG. 3 is a graphical representation of the amount of active hypochlorite remaining in solution as a function of time for solutions initially set at different starting pHs.

Sodium hypochlorite was added at a final concentration of 3.5 mM (approximately 250 ppm chlorine) to three identical saline solutions containing 125 mM NaCl, 1 mM $Na_2S_2O_3$ and 5 mM $Na_2HPO_4$. The mole ratio of 1 mM $Na_2S_2O_3$; 3.5 mM NaOCl was chosen within the constraints of Example 1. The concentration of dibasic sodium phosphate pre-buffer was chosen for achieving neutral pH with the acid produced by the reaction of the above-concentrations of NaOCl and $Na_2S_2O_3$. Each of the three reaction mixtures maintained at room temperature (23° C.) was adjusted to a different starting pH with HCl or NaOH to illustrate how increasing or decreasing the initial reaction pH can be used to respectively lengthen or shorten the lifetime of the hypochlorite in solution. The time course of these three reactions is shown in FIG. 3 (curve 1, pH 9.85; curve 2, pH 10.11; curve 3, pH 10.31). Hypochlorite levels (solid line curves), pH levels (dashed line curves).

Table I below summarizes the pH and hypochlorite levels as a function of time for the curves shown in FIG. 3. The amount of hypochlorite present in the reaction solution upon initial miing has been defined as 100%. It is evident that hypochlorite lifetime could be approximately doubled with each of these pH increases, ie. from approximately 8 min (pH 9.85) to 16.5 min (pH 10.11) to 31 min (pH 10.31). The pHs of the three completed reaction solutions became essentially identical due to the generation of binary phosphate buffer from simple dibasic sodium phosphate during the course of the reaction.

TABLE I

| TIME (min) | pH | NaOCl (%) | TIME (min) | pH | NaOCl (%) | TIME (min) | pH | NaOCl (%) |
| --- | --- | --- | --- | --- | --- | --- | --- | --- |
| 0 | 9.85 | 100 | 0 | 10.11 | 100 | 0 | 10.31 | 100 |
| 1.5 | 9.75 | 99 | 5.0 | 9.98 | 99 | 5.0 | 10.24 | 99 |
| 3.0 | 9.61 | 97 | 9.5 | 9.80 | 97 | 10.0 | 10.16 | 97 |
| 5.0 | 9.32 | 93 | 12.0 | 9.61 | 96 | 15.0 | 10.07 | 96 |
| 6.0 | 8.91 | 89 | 14.5 | 9.20 | 92 | 20.0 | 9.95 | 94 |
| 6.5 | 8.50 | 79 | 15.3 | 8.82 | 86 | 27.0 | 9.52 | 87 |
| 6.8 | 8.20 | 66 | 15.7 | 8.40 | 74 | 29.5 | 9.00 | 79 |
| 7.3 | 7.63 | 34 | 16.0 | 7.50 | 37 | 30.5 | 8.20 | 63 |
| 8.0 | 7.02 | 0 | 16.5 | 7.08 | 2 | 30.8 | 7.80 | 39 |
|  |  |  | 16.8 | 7.00 | 0 | 31.0 | 7.20 | 8 |
|  |  |  |  |  |  | 31.5 | 7.00 | 0 |

EXAMPLE 4

Table II below illustrates that the mole ratio of thiosulfate to hypochlorite in the reaction mixture affects the lifetime of the hypochlorite, and the initial and final pHs of the solution.

Three identical saline solutions were prepared containing 125 mM NaCl, 10 mM $Na_2HPO_4$ (pre-buffer) and 7 mM NaOCl (1:100 dilution of a 5.25% NaOCl solution titrated to pH 10.0). Either 2.0, 3.0 or 4.0 mM $Na_2S_2O_3$ was added to each solution. Hypochlorite levels (determined as in Example 1) and pHs were monitored during the course of these reactions. Initial solution pH measurements were obtained immediately after adding the thiosulfate. Final pHs were obtained after all hypochlorite had been consumed. Hypochlorite lifetimes represent times between adding the thiosulfate and detecting no residual hypochlorite in the solutions.

TABLE II

|  | mM Ratio Thiosulfate:Hypochlorite | | |
| --- | --- | --- | --- |
|  | 2.0:7.0 | 3.0:7.0 | 4.0:7.0 |
| Initial pH | 10.43 | 10.68 | 10.85 |
| Final pH | 6.98 | 7.26 | 7.60 |
| NaOCl lifetime (min) | 18 | 27 | 85 |

EXAMPLE 5

Achieving controlled hypochlorite lifetime and neutral final pH for a wide range hypochlorite concentrations is shown in this set of experiments.

By first establishing an appropriate ratio of thiosulfate: hypochlorite: pre-buffer, then maintaining this ratio approximately constant when employing differing concentrations of hypochlorite, and finally by adjusting the initial pH of the particular reaction mixture, the hypochlorite lifetime and pH of the completed reaction solution are controlled. For example, an increase in the initial reaction pH is often required to maintain a constant exposure interval to hypochlorite when increased hypochlorite concentrations are utilized. Increased pre-buffer concentrations may also be required to reach a constant final pH when increased concentrations of hypochlorite and thiosulfate are utilized.

Figure 4:
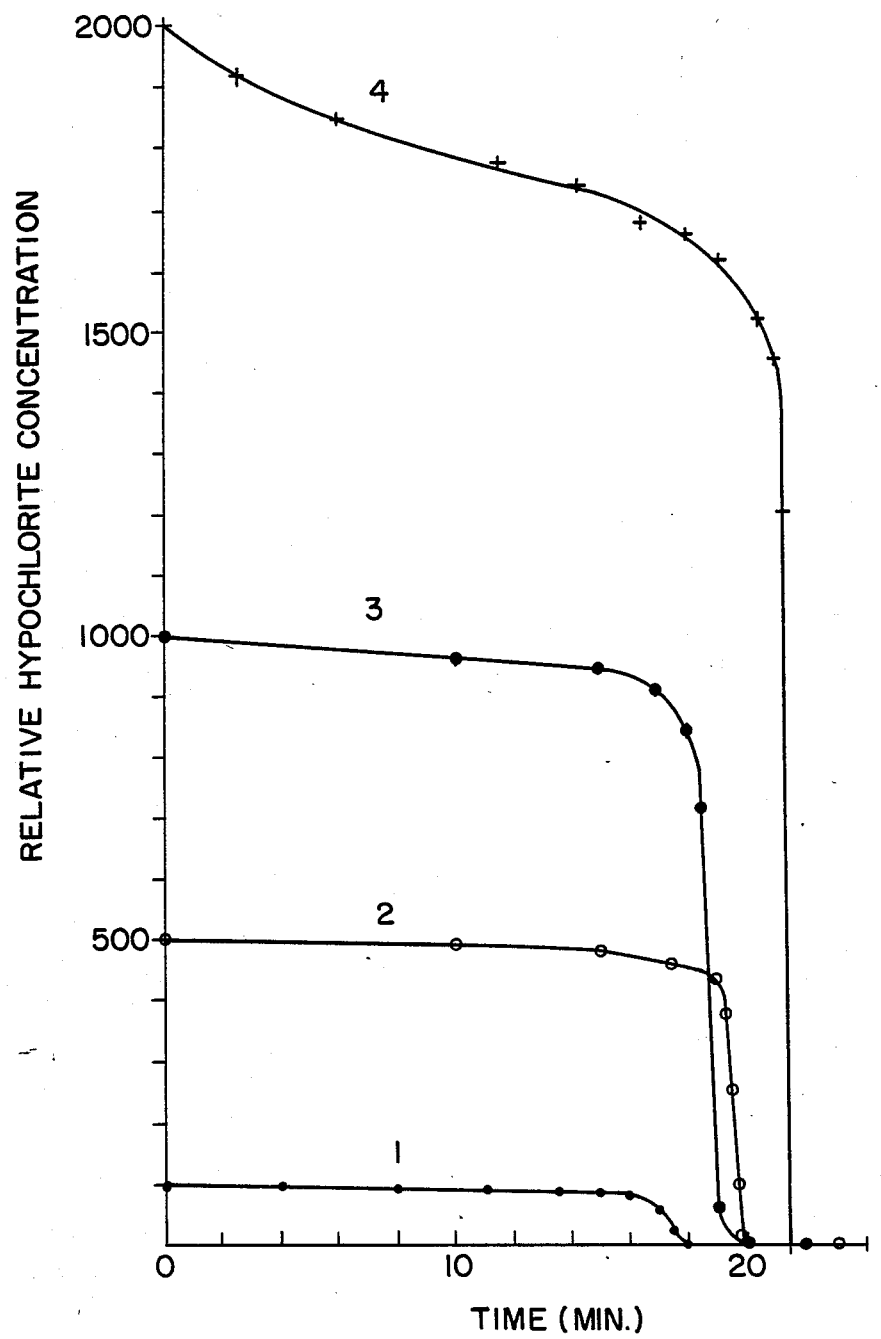
FIG. 4 is a graphical representation of the hypochlorite concentration as a function of the time for solutions containing different initial amounts of hypochlorite and thiosulfate with these solutions set at different starting pHs.

The following four reactions illustrate how hypochlorite lifetime can be kept relatively constant despite great changes in reactant concentrations by adjusting the initial pH of the reaction solution. In these reactions, the thiosulfate: hypochlorite: pre-buffer concentration ratios are maintained constant. With each reaction, the saline, thiosulfate, and $Na_2HPO_4$ pre-buffer were combined in a volume of 20 ml at 23° C. Concentrated hypochlorite (5.25%, pH 10.0) was then added and the reaction solution titrated with HCl or NaOH to the pH indicated at time zero. Samples were removed during the course of the reactions for iodimetry as in Example 1 and solution pHs were monitored continuously. Table III summarizes the reaction conditions, pH parameters and hypochlorite lifetimes. FIG. 4 illustrates the rates of hypochlorite consumption in the four reactions (reaction number in Table II corresponds to curve number in FIG. 4). The relative hypochlorite concentrations shown in FIG. 4 are based on the initial concentrations added to the respective reactions. The most concentrated NaOCl-containing solution (28 mM) has an active chlorine content of approximately 2000 ppm and is so indicated in FIG. 4.

TABLE III

| Reaction Compositions and Parameters | | | | |
| --- | --- | --- | --- | --- |
|  | Initial Concentration (mM) | | | |
|  | Reaction 1 | Reaction 2 | Reaction 3 | Reaction 4 |
| INGREDIENT |  |  |  |  |
| NaCl | 125 | 125 | 125 | 125 |
| $Na_2HPO_4$ | 2 | 10 | 20 | 40 |
| $Na_2S_2O_3$ | 0.4 | 2 | 4 | 8 |
| NaOCl | 1.4 | 7 | 14 | 28 |
| PARAMETER |  |  |  |  |
| Initial pH | 9.90 | 10.26 | 10.41 | 10.75 |
| Final pH | 7.16 | 7.05 | 7.07 | 7.19 |

TABLE III-continued

| | Reaction Compositions and Parameters | | | |
| --- | --- | --- | --- | --- |
| | Initial Concentration (mM) | | | |
| | Reaction 1 | Reaction 2 | Reaction 3 | Reaction 4 |
| NaOCl Lifetime | 18 min | 21 min | 20 min | 21 min |

EXAMPLE 6

Cold sterilization of aerosol saline solutions in nitrogen-pressurized aluminum aerosol canisters using approximately 500 ppm hypochlorite is shown.

In the prior art, buffered and unbuffered saline solutions have been sterile-packaged in aerosol canisters. The use of such hermetically sealed aerosol packaging obviates the need for chemical preservatives to maintain sterility of the saline formulation. Currently sterilization of such aerosol canisters is achieved using ionizing radiation. While this process is effective and FDA approved, it is costly. The chemistry of the present invention achieving delayed neutralization of hypochlorite, non-toxic chemical products and neutral final pH has the potential of sterilizing aerosol canister contents in situ. By adding agents of the present invention at the time of canister filling, the need to use ionizing radiation to achieve sterility can be eliminated.

The ability of solutions of the present invention to render sterile both a saline solution and the aerosol canister holding that solution was demonstrated by the following procedure and using the following solutions:

| SOLUTION (1) Prepare 1 kg of the following: | |
| --- | --- |
| | % w/w |
| Sodium chloride | 0.8116 |
| Sodium phosphate dibasic anhydrous | 0.2367 |
| Sodium thiosulfate, anhydrous | 0.0351 |
| deionized water | q.s. to 1000 gm |
| Solution pH 8.9–9.1 | |

Solution (1—1): Transfer 500 gm of solution (1) into a beaker and adjust pH to 7.1 with 1N HCl solution.

Solution (2): Prepare an aqueous bacterial spore suspension with a volume of 10 ml consisting of approximately $5 \times 10^7$ spores per ml of *Bacillus subtilis* var. *niger* (BSN).

Solution (3): Titrate a fresh alkaline solution of 0.525% sodium hypochlorite (pH~11) to pH 10.00 using 1N HCl. Prestandardize pH meter electrode with a pH 7.00 standard buffer.

Solution (4): To each of three identical standard aluminum canisters ($1\frac{3}{4}'' \times 4\frac{1}{2}''$), add 94.5 gm of solution (1), 1 gm of solution (2) and 10.5 gm of solution (3). Crimp and pressurize the cans to 100 psig with nitrogen. Shake the cans for 60 seconds and discharge each can for 2 sec to fill the aerosol valve assemblies and to contact the internal surfaces of the aerosol canisters.

Solution (5): As an unsterilized control, add 94.5 gm solution (1—1), 1 gm solution (2) and 10.54 gm of water. Crimp, pressurize, shake and discharge this canister as for solution (4).

All canisters including their actuators are immersed in a clorox bath (approximately 50 ppm active chlorine) for 5 min to disinfect the outside of the aerosol cans. Subsequently standardized USP sterility tests were performed on the discharged solution contents of the above aerosol solutions. Culturing tests were continued for 14 days.

The Results: All samples cultured from the three aerosol canisters of solution (4) were sterile after both 7 and 14 days incubation. All control samples cultured from the aerosol canister of solution (5) lacking hypochlorite were heavily contaminated with BSN indicating a concentration of approximately $5 \times 10^5$ spore cfu per ml in solution (5).

In a separate experiment discharged samples from an aerosol canister holding solution (4) were harvested over a period of 30 minutes following mixing of the original solution. Hypochlorite remaining in each sample was neutralized upon discharge using excess sodium thiosulfate. The samples were each cultured to detect residual viable BSN cells.

The data were as follows:

| | Hypochlorite exposure time (min) | | | | | | |
| --- | --- | --- | --- | --- | --- | --- | --- |
| | 0 | 1 | 2 | 3 | 5 | 10 | 30 |
| BSN cfu per ml: | $8 \times 10^4$ | $3.8 \times 1^4$ | $4.0 \times 10^1$ | 0 | 0 | 0 | 0 |

This experiment demonstrates that approximately 3 minutes are required to obtain a 5 log reduction in viable spore count.

What is claimed:

1. A process for disinfecting, sterilizing, bleaching and/or cleansing a liquid or a surface comprising:
    producing an aqueous solution of hypochlorite, an alkali metal or alkaline earth thiosulfate and a prebuffer wherein the hypochlorite has an initial concentration of about 5–5,000 parts per million available chlorine and the molar ratio of thiosulfate to hypochlorite is between 0.25 to 1 and 0.75 to 1;
    adjusting the initial pH of the solution to between 9.0 and 11.0;
    contacting the surface or liquid with the solution until the hypochlorite is consumed, wherein the prebuffer allows the pH of the solution to decrease as the hypochlorite is consumed by the thiosulfate, the lifetime of the hypochlorite being dependent on the initial pH of the solution.

2. The process according to claim 1 wherein said prebuffer is selected from the group consisting of dibasic alkali metal phosphates, alkali metal borates and alkali metal carbonates.

3. The process according to claim 1 wherein the hypochlorite is selected from the group consisting of inorganic hypochlorite, chlorine and N-chloro compounds and combinations thereof.

4. The process according to claim 1 wherein the initial pH of the solution is in the range of 9.0 to 11.0 and the final pH of the solution is between 6.0 and 8.0.

5. The process according to claim 1 further comprising:
    adding up to 1% NaCl to the solution.

6. The process according to claim 1 further comprising:
    adding a detergent to the initial solution wherein the detergent is unreactive with the hypochlorite.

7. The process according to claim 1 further comprising:
    adding a pH indicator to the initial solution wherein the pH indicator is unreactive with the hypochlorite.

8. The process according to claim 1 wherein the consumption of hypochlorite occurs in ranges from 30 seconds to 3 hours.

9. The process according to claim 1 wherein said solution is produced by dispersing or dissolving a formulation comprising a hypochlorite producing compound, a thiosulfate and a prebuffer said formulation being in liquid, powder or tablet form.

10. An aqueous disinfecting, sterilizing, bleaching and/or cleansing solution comprising:
hypochlorite of between 0.0004% and 0.5% by weight;
an alkali metal or alkaline earth thiosulfate wherein the molar ratio of the thiosulfate to the hypochlorite is between 0.25 and 1 and 0.75 to 1;
a prebuffer;
wherein the initial pH of the solution is set to a value of between 9.0 and 11.0 and the pH of the solution subsequently decreases as the hypochlorite is consumed by the thiosulfate, the lifetime of the hypochlorite being dependent on the initial pH of the solution.

11. The solution according to claim 10 wherein said prebuffer is selected from the group consisting of dibasic alkali metal phosphates, alkali metal borates and alkali metal carbonates.

12. The solution according to claim 10 wherein the hypochlorite is selected from the group consisting of inorganic hypochlorite, chlorine and N-chloro compounds.

13. The solution according to claim 10 wherein the initial pH of the solution is in the range of 9.0 to 11.0 and the final pH of the solution is in the range of 6.0 to 8.0.

14. The solution according to claim 10 further comprising up to 1% NaCl by weight.

15. The solution according to claim 10 further comprising a detergent which is unreactive with the hypochlorite.

16. The solution according to claim 10 further comprising a pH indicator which is unreactive with the hypochlorite.

17. The solution according to claim 10 wherein the active hypochlorite in the solution lasts from 30 seconds to 3 hours.

18. A process for controlling hypochlorite lifetime comprising:
producing an aqueous solution of hypochlorite wherein the concentration of hypochlorite is between 0.0004% and 0.5% by weight, alkali metal or alkaline earth thiosulfate and a prebuffer, wherein the initial molar ratio of thiosulfate to hypochlorite is between 0.25 to 1 and 0.75 to 1;
adjusting the initial pH of said solution to between 9.0 and 11.0 wherein the prebuffer has a pKa less than the initial pH of said solution;
contacting the liquid or surface with said solution until the hypochlorite is consumed, wherein the prebuffer allows the pH of the solution to decrease, the final pH of said solution being stabilized by buffer produced from said prebuffer, and wherein the hypochlorite lifetime is dependent on the initial pH of said solution.

19. The process according to claim 18 wherein the hypochlorite is selected from the group consisting of alkali metal and alkaline-earth hypochlorites.

20. The process according to claim 18 further comprising: adding up to 1% NaCl to the solution.

21. The process according to claim 18 further comprising:
adding a detergent to the solution wherein the detergent is unreactive with the hypochlorite.

22. The process according to claim 18 further comprising:
adding a pH indicator to the solution wherein the pH indicator is unreactive with the hypochlorite.

23. The process according to claim 18 wherein the consumption of hypochlorite occurs in ranges from 30 seconds to 3 hours.

24. The process according to claim 18 wherein said initial solution is produced by dispersing or dissolving a formulation comprising a hypochlorite producing compound, a thiosulfate and a prebuffer said formulation comprising a hypochlorite producing compound, a thiosulfate and a prebuffer said formulation being in liquid, powder or tablet form.

25. The process according to claim 1 further comprising:
packaging and sealing said solution in an aerosol container before the hypochlorite is consumed.

26. The process of claim 25 further comprising:
pressurizing said aerosol container;
filling an aerosol valve assembly of said container and shaking said container, thereby contacting the internal surfaces of said container and said valve assembly before the hypochlorite is consumed.

* * * * *